United States Patent [19]

Heywang et al.

[11] 4,305,112
[45] Dec. 8, 1981

[54] CAPACITANCE HUMIDITY SENSING ELEMENT

[75] Inventors: Hermann Heywang, Munich; Johann Kammermaier, Unterhaching; Joachim Rauhut, Munich, all of Fed. Rep. of Germany

[73] Assignee: Siemens Aktiengesellschaft, Berlin & Munich, Fed. Rep. of Germany

[21] Appl. No.: 90,051

[22] Filed: Oct. 31, 1979

[30] Foreign Application Priority Data

Nov. 6, 1978 [DE] Fed. Rep. of Germany ....... 2848034

[51] Int. Cl.³ .............................................. H01G 7/00
[52] U.S. Cl. .................................... 361/286; 73/336.5
[58] Field of Search ...................... 361/286, 311, 306; 73/336.5

[56] References Cited

U.S. PATENT DOCUMENTS

| | | | |
|---|---|---|---|
| 2,627,645 | 2/1953 | Harris | 361/311 |
| 2,884,593 | 4/1959 | Miyata | 361/286 X |
| 3,360,701 | 12/1967 | Dornfeld | 361/306 X |
| 3,550,941 | 11/1967 | Misevich | |
| 3,582,728 | 6/1971 | Thoma | 73/336.5 X |

FOREIGN PATENT DOCUMENTS 2702487 7/1977 Fed. Rep. of Germany .
1418388 12/1975 United Kingdom .

*Primary Examiner*—Elliot A. Goldberg
*Attorney, Agent, or Firm*—Hill, Van Santen, Steadman, Chiara & Simpson

[57] ABSTRACT

A multi-layered capacitive humidity sensing element having a carrier material separated from a water vapor permeable, electrically conductive coating by an insulating layer which is humidity sensitive, and a method for its manufacture is provided. A metal foil is utilized as the carrier material serving both as a support frame and as an electrically conductive layer. A thin gold layer is applied to the insulating layer, which is formed out of a synthetic material. The gold layer is sufficiently permeable to allow water vapor to freely diffuse into the synthetic layer from the surrounding atmosphere, yet remains thick enough to function as an electrically conductive outer layer. The sensing element thus constructed has both a short response time and an improved simplicity of manufacture.

4 Claims, 2 Drawing Figures

CAPACITANCE HUMIDITY SENSING ELEMENT

BACKGROUND OF THE INVENTION

1. Field of the Invention

The present invention relates to a capacitive humidity sensing element, and more particularly to such an element that is multi-layered and which contains a carrier material insensitive to humidity, having at least one humidity-sensitive layer, and at least one water vapor permeable, electrically conductive coating bonded to the carrier.

2. Description of the Prior Art

A capacitive humidity sensing element is known from U.S. Pat. No. 3,350,941. Therein, a carrier consisting of a non-electrically conductive material which is also not sensitive to humidity, i.e., the ambient water vapor, is attached to a support frame. Humidity sensitive layers are applied to both sides of this carrier. The humidity sensitive layers are in turn coated with sprayed-on, electrically conductive layers. These form the coatings of the capacitor and contacts are provided at the support frame. This construction is relatively involved and does not permit the economical mass production of this device.

SUMMARY OF THE INVENTION

The present invention thus has as an underlying objective, the provision of a humidity sensing element of the type previously described which has both a short response time, while also capable of serially manufactured with a minimum outlay.

These objectives are resolved by the provision of such a humidity sensing element having a metal foil carrier, at least one humidity sensitive layer arranged thereon, and a humidity-permeable metal layer arranged above the humidity sensitive layer. A synthetic layer is meant to describe a layer composed of a polymerized synthetic material. A mono-molecular layer is not a synthetic layer within the meaning ascribed by the present invention.

A particularly sturdy embodiment is obtained when the synthetic layer is a polyimide foil and is bonded to the metal foil by a thin adhesive layer. A polysulfone resin is also well suited as the synthetic layer, which may likewise advantageously be glued on. A metal foil consisting of a rust-resistant, iron-nickel-chromium-steel is particularly appropriate as the metal foil for a couple of reasons. This metal produces a particularly smooth surface which allows the adhesive layer to be kept very thin, and thus exert no significant influence on the humidity sensitivity of the dielectric. Additionally, such an alloy steel does not become oxidized or corroded in some manner during extended operation of the humidity sensing element.

The synthetics can also be directly applied to the metal foil in a dissolved form as a lacquer. For this method given polyimide, one accordingly proceeds as follows: first, a soluble polyimide preliminary coating is applied to the metal foil in a lacquering operation; the solvent is subsequently removed from the lacquer layer by drying; and the metal foil coated in this manner is tempered at a temperature of at least 275° C., whereby the components responsible for the solubility of the polyimide preliminary stage are pyrolitically volatilized and insoluble polyimide layers are formed whose chemical composition and sensitivity to humidity correspond to unsupported polyimide foils. This method is known, however it is advantageous in the present invention that the tempering process required for the manufacture of the thin polyimide lacquer layers can be carried out without thermal damage of the carrier foil, since it consists of metal. Polyimide is particularly well suited for the manufacture of capacitive humidity sensing elements because its dielectric constant increases linearly with the relative air humidity, and is only slightly influenced by the environmental temperature. In this manner, layers of polyimide can be manufactured with thicknesses below 5 μm. These vary small layer thicknesses result in the manufacture of humidity sensing elements which respond especially quickly to changes in humidity.

The metal layer forming the second coating advantageously consists of a thin gold layer through which the water vapor can pass without any significant resistance. Below a coating thickness of approximately 5 nm, gold layers consist of particles which are arranged island-like but which are nonetheless conductively connected because of tunnel effects. Between these grouped particles, water molecules can diffuse without obstruction either into the synthetic layer or from the synthetic layer into the surrounding air.

Electrical connections for the contacting can be manufactured on this gold layer with a particularly low outlay by having the electric connection wire bonded to the metal layer by an electrically conductive epoxy resin compound which is capable of being applied by silk screening. Such electrically conductive epoxy resin compounds generally contain finely distributed metal or, also, finely distributed carbon particles or the like for producing the conductivity. The degree conductivity is sufficient for the load required here. The adhesion of such an epoxy resin compound is particularly good in the present case, since the adhesion can ensue to the synthetic through the gold layer.

Conventional connections such as bonded, welded, or soldered connections may also be utilized with the thin gold electrode where the portion of the electrode adjacent to the connection is strengthened.

In order to achieve particularly short response times, a thin, water vapor-permeable gold layer is first applied to the carrier. Next, a humidity-sensitive synthetic layer followed by a second water vapor-permeable gold layer is applied. A part of the carrier is then etched away in such manner that the remaining part of the carrier forms a partially dissolved support frame for the synthetic layer with the gold electrodes. Given this structural form, layers which are not self-supporting because of their thinness can be employed, since no stressing of the component part due to fabrication operations occurs after the etching of the corresponding areas of the metal carrier foil. The supportive frame remaining has sufficient mechanical stability for the post-manufacturing manipulations and handling associated with its employment. This very significantly shortens the response time of the humidity sensing element, since the response time is proportional to the square of the length of the diffusion path of the $H_2O$ molecules proceeding in the normal direction within the synthetic layer. Given atmospheric access at both sides, this length is equal to half the synthetic layer thickness.

The present inventive humidity sensing element is able to be manufactured particularly economically where the humidity-sensitive layers and the metal layers are applied to a metal foil in an applied tape-type operation, with the continuous tape subsequently separated into individual humidity sensing elements. With the method, the synthetic layer can be applied continuously, while the precious metal layer is advantageously vapor-deposited in the locations and amounts required in the humidity sensing element, with the remaining areas covered. The covering can ensue by means of moving screens.

Various other objects, advantages, and features of the present invention will become readily apparent from the ensuing detailed description and drawings, with the novel features particularly pointed out in the appended claims.

DESCRIPTION OF THE PREFERRED EMBODIMENTS

Figure 1:
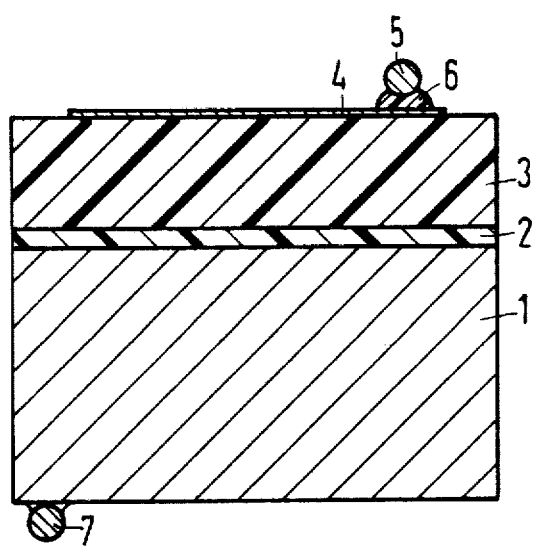
FIG. 1 is a sectional view showing an embodiment of the present invention.

In FIG. 1, a synthetic layer 3 and a gold electrode layer 4 materially bonded to it, are glued to a metal foil 1 by means of an adhesive layer 2. The synthetic layer 3 can also be lacquered onto the metal foil 1. A contacting wire 5 is electrically conductively connected to the gold layer 4 by means of an electrically conductive—epoxy resin compound 6. A second contacting wire 7 is soldered to the metal foil 1.

Figure 2:
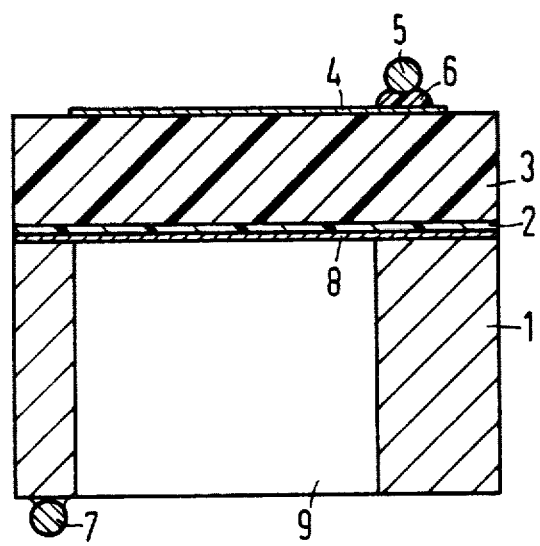
FIG. 2 is a view similar to FIG. 1 showing an alternate embodiment of the present invention.

In the embodiment shown in FIG. 2 (identical reference numerals maintained where the structure is unchanged), a gold layer 8 is first applied to the metal foil 1. A synthetic layer 3 with gold electrode layer 4 is applied to the gold layer 8 using an adhesive layer 2. An opening 9 is then etched into the metal foil 1. The then remaining portions of the metal foil 1 serve as the support frame for the layers 2-4, and 8 which remain after the etching.

We claim as our invention:

1. An improved capacitive humidity sensing element of the type in which a carrier consisting of a material which is not humidity sensitive is separated from a water-vapor permeable, electrically conducting coating by a humidity sensitive, insulating layer attached to said carrier wherein the improvement comprises:
   said carrier is a rust-resistant, iron-chromium-nickel steel foil; and
   at least one humidity sensitive polyimide foil, having at least one water-vapor permeable metal layer arranged thereon, is attached to said carrier by a thin adhesive layer.

2. An improved capacitive humidity sensing element of the type in which a carrier consisting of a material which is not humidity sensitive is separated from a water-vapor permeable, electrically conducting coating by a humidity sensitive, insulating layer attached to said carrier wherein the improvement comprises:
   said carrier is a rust-resistant, iron-chromium-nickel steel foil; and
   at least one humidity sensitive polysulfone foil, having at least one water-vapor permeable metal layer arranged thereon, is attached to said carrier by a thin adhesive layer.

3. A capacitive humidity sensing element as described in claim 1 or 2 wherein said metal layer is a gold layer of sufficient thickness to allow water vapor to pass therethrough without significant resistance.

4. A capacitive humidity sensing element as described in claim 1 or 2 and further comprising:
   an electric connection wire attached to said metal layer by means of a silk-screenable, electrically conductive, epoxy resin compound.

* * * * *